(12) United States Patent
Henderson et al.

(10) Patent No.: US 11,512,417 B2
(45) Date of Patent: Nov. 29, 2022

(54) ENZYME-RESPONSIVE SHAPE MEMORY POLYMERS

(71) Applicants: James Henderson, Syracuse, NY (US); Patrick T. Mather, Lewisburg, PA (US); Shelby Buffington, Syracuse, NY (US)

(72) Inventors: James Henderson, Syracuse, NY (US); Patrick T. Mather, Lewisburg, PA (US); Shelby Buffington, Syracuse, NY (US)

(73) Assignee: SYRACUSE UNIVERSITY, Syracuse, NY (US)

( * ) Notice: Subject to any disclaimer, the term of this patent is extended or adjusted under 35 U.S.C. 154(b) by 625 days.

(21) Appl. No.: 16/367,473

(22) Filed: Mar. 28, 2019

(65) Prior Publication Data

US 2019/0301064 A1    Oct. 3, 2019

Related U.S. Application Data

(60) Provisional application No. 62/649,934, filed on Mar. 29, 2018.

(51) Int. Cl.
| | |
|---|---|
| *D04H 1/4358* | (2012.01) |
| *D04H 1/728* | (2012.01) |
| *D04H 1/435* | (2012.01) |
| *D04H 1/4382* | (2012.01) |
| *C12N 5/00* | (2006.01) |

(52) U.S. Cl.
CPC ......... *D04H 1/4358* (2013.01); *C12N 5/0018* (2013.01); *D04H 1/435* (2013.01);
(Continued)

(58) Field of Classification Search
CPC .. D04H 1/4358; D04H 1/43835; D04H 1/435; D04H 3/011; D10B 2401/046
(Continued)

(56) References Cited

U.S. PATENT DOCUMENTS 5,700,337 A * 12/1997 Jacobs ................ B32B 27/281
156/64
2005/0208860 A1* 9/2005 Baron .................... A41D 27/28
442/374
(Continued)

OTHER PUBLICATIONS

Ping, Peng, et al. "Poly(ε-Caprolactone) Polyurethane and Its Shape-Memory Property." Biomacromolecules, vol. 6, No. 2, Jan. 14, 2005, pp. 587-592., doi:10.1021/bm049477j. (Year: 2005).*
(Continued)

*Primary Examiner* — Larissa Rowe Emrich
(74) *Attorney, Agent, or Firm* — David Nocilly

(57) ABSTRACT

An enzyme responsive shape memory polymer formed from a glassy, cross-linked shape memory polymer that incorporates ester bonds that are responsive to the present of an enzyme. PCL-based polyurethanes (featuring simple alternation of PCL diol and lysine-based diisocyanate) are degradable by Amano lipase PS. A non-degradable thermoplastic elastomer may be dual electrospun with a polycaprolactone based TPU with the fixing phase compressed so that the composite is ready for enzymatically triggered contraction. Alternatively, the elastomer may be a PCL copolymer-based polyurethane amorphous elastomer that is both degradable and elastomeric and put into compression so that upon enzymatic degradation of the elastomeric phase the scaffold expands.

12 Claims, 12 Drawing Sheets

(52) U.S. Cl.
CPC ......... *D04H 1/43835* (2020.05); *D04H 1/728* (2013.01); *C12N 2500/50* (2013.01); *D10B 2401/046* (2013.01); *D10B 2401/12* (2013.01)

(58) Field of Classification Search
USPC .................................. 442/414, 415; 428/913
See application file for complete search history.

(56) References Cited

U.S. PATENT DOCUMENTS

| | | | | |
|---|---|---|---|---|
| 2010/0172952 | A1* | 7/2010 | Srouji | A61P 19/00 424/423 |
| 2011/0059527 | A1* | 3/2011 | Mather | C08J 3/246 435/395 |
| 2012/0225600 | A1* | 9/2012 | Rule | B29C 61/02 442/328 |
| 2014/0135454 | A1* | 5/2014 | Mather | C08G 18/4833 525/418 |
| 2015/0038038 | A1* | 2/2015 | Korley | A61L 31/16 442/166 |

OTHER PUBLICATIONS

"Calendering-Grade TPU." Nonwovens Industry Magazine—News, Markets Analysis for the Nonwovens Industry, Nov. 30, 2001, www.nonwovens-industry.com/contents/view_breaking-news/0000-00-00/calendering-grade-tpu/. (Year: 2001).*

* cited by examiner

ENZYME-RESPONSIVE SHAPE MEMORY POLYMERS

CROSS-REFERENCE TO RELATED APPLICATIONS

The present application claims priority to U.S. Provisional No. 62/649,934, filed on Mar. 29, 2018.

STATEMENT REGARDING FEDERALLY SPONSORED RESEARCH OR DEVELOPMENT

This invention was made with government support under Grant No. 1609523 awarded by the National Science Foundation (NSF). The government has certain rights in the invention.

BACKGROUND OF THE INVENTION

1. Field of the Invention

The present invention relates to shape memory polymers and, more particularly, to shape memory polymers that are responsive to biological stimuli.

2. Description of the Related Art

The study of the interface of synthetic materials and living systems has largely been limited to "one way" phenomena, such as cellular response to material chemistry, modulus, or topography, material degradation, or implanted materials. Studies of stimuli responsive materials that respond to local environmental cues-pH, ionic strength, temperature, light, oxidation/reduction state, or the presence of small molecules or enzymes have also remained essentially one way. Cytocompatible shape memory polymers activated by thermal or photothermal triggers have been developed and established as powerful "smart material" platforms for both basic and translational research. However, there are no known enzyme-responsive shape memory polymers. Accordingly, there is a need in the art for shape memory polymers that can respond to enzymatic stimuli and can do so under isothermal cell culture conditions.

BRIEF SUMMARY OF THE INVENTION

The present invention integrates stimuli responsive biomaterials with biological systems to create hybrid feedback systems that can provide new insight into phenomena at the interface of synthetic/living material systems. More specifically, the present invention includes enzyme-responsive shape-memory polymers that can be used for innovative synthetic/living feedback systems.

In a first embodiment, the present invention comprises a shape memory polymer that is responsive to an enzyme. The shape memory polymer is a composite fiber mat formed from at least a first set of fibers that are intermingled with a second set of fibers, wherein the first set of fibers are formed from a first polymer having a transition temperature such that the fiber web can be fixed into a temporary shape when the fiber web is above the transition temperature and will remain in the temporary shape when the fiber web is below the transition temperature, wherein the second set of fibers are formed from a second polymer that will apply a biasing force to the first set of fibers when the fiber web is fixed into the temporary shape and the fiber web is below the transition temperature, and wherein the first polymer is degradable by the enzyme and the second polymer is not degradable by the enzyme. The first polymer may be a thermoplastic polyurethane such as poly(ε-caprolactone). The second polymer may be an aromatic polyether-based thermoplastic polyurethane (TPU) such as PELLETHANE® 5863-80A. The fiber web may comprise between about 20 percent and about 50 percent poly(ε-caprolactone) by mass.

In another embodiment, the present invention may be a method of forming a shape memory polymer that is responsive to an enzyme. The method includes providing a first polymer that is degradable by the enzyme and has a transition temperature, providing a second polymer that is not degradable by the enzyme, and then dual electrospinning a first solution containing the first polymer with a second solution containing the second polymer to form a composite fiber mat formed at least a first set of fibers of the first polymer intermingled with at least a second set of fibers of the second polymer and that has an initial shape. The composite fiber mat may be heated above the transition temperature of the first polymer and then fixed into a temporary shape so that the second set of fibers apply a biasing force to the first set of fiber. The method may also include the step of exposing the composite fiber mat to the enzyme so that the first set of fibers are degraded, thereby allowing the second set of fibers to return the fiber mat from the temporary shape.

The present invention demonstrate enzymatic recovery, as contraction of tensile specimens, using bulk enzymatic degradation experiments and show that shape recovery is achieved by degradation of the PCL shape-fixing phase. The present invention and the process of enzymatic shape recovery are cytocompatible. Thus, the SMP design of the present invention represents both an enzyme responsive material capable of applying a programmed shape change or direct mechanical force and an SMP that could respond directly to biological activity.

The stimuli responsive shape-memory polymers of the present invention are significant because they can provide new fundamental materials understanding of a specific class of stimuli responsive materials—shape-memory polymers—while also broadly impacting understanding of synthetic/living systems through discovery of new material phenomena. Such understanding can to have broad impact in applications in which synthetic stimuli responsive materials are designed to contact biological systems. Specific examples of such transformative outcomes would include: drug delivery vehicles that affect the target cells/organs through controlled release that is modulated by the physiological status of the cells/organs; scaffolds that guide tissue regeneration through alterations in material and mechanical properties that are modulated by properties and behavior of the regenerating tissue; platforms for stem cell culture that present a tailored microenvironment to maintain stem cell phenotype or, alternatively, to differentiate cells down a specific lineage in response to the phenotypic state of the cells; and decision-making ("sense and treat") biosensors that use feedback systems to control patient treatment. Thus, the outcomes are not only expected to provide fundamental advances in the field of biomaterials, but also to have broad societal impact through breakthroughs that can be anticipated in diverse bioengineering and healthcare fields.

BRIEF DESCRIPTION OF THE SEVERAL VIEWS OF THE DRAWING(S)

The present invention will be more fully understood and appreciated by reading the following Detailed Description in conjunction with the accompanying drawings, in which:

FIG. 1 is a schematic of enzyme responsive shape memory polymers and the use of such polymers in fully autonomous feedback system according to the present invention based on photo-thermal shape memory polymer uses.

FIG. 2 is a schematic of an embodiment of an enzyme responsive shape memory polymer according to the present invention; and FIG. 3 is a demonstration of successful enzymatic shape recovery for a fiber composite composed of 20:80 PCL: PELLETHANE®, where the sample at left was incubated in a solution of 1 mg/mL lipase and enzymatically triggered to return to its original shape and the control sample at right was incubated in PBS and experienced no shape change.

Figures 9A, 9B, 9C, 9D:
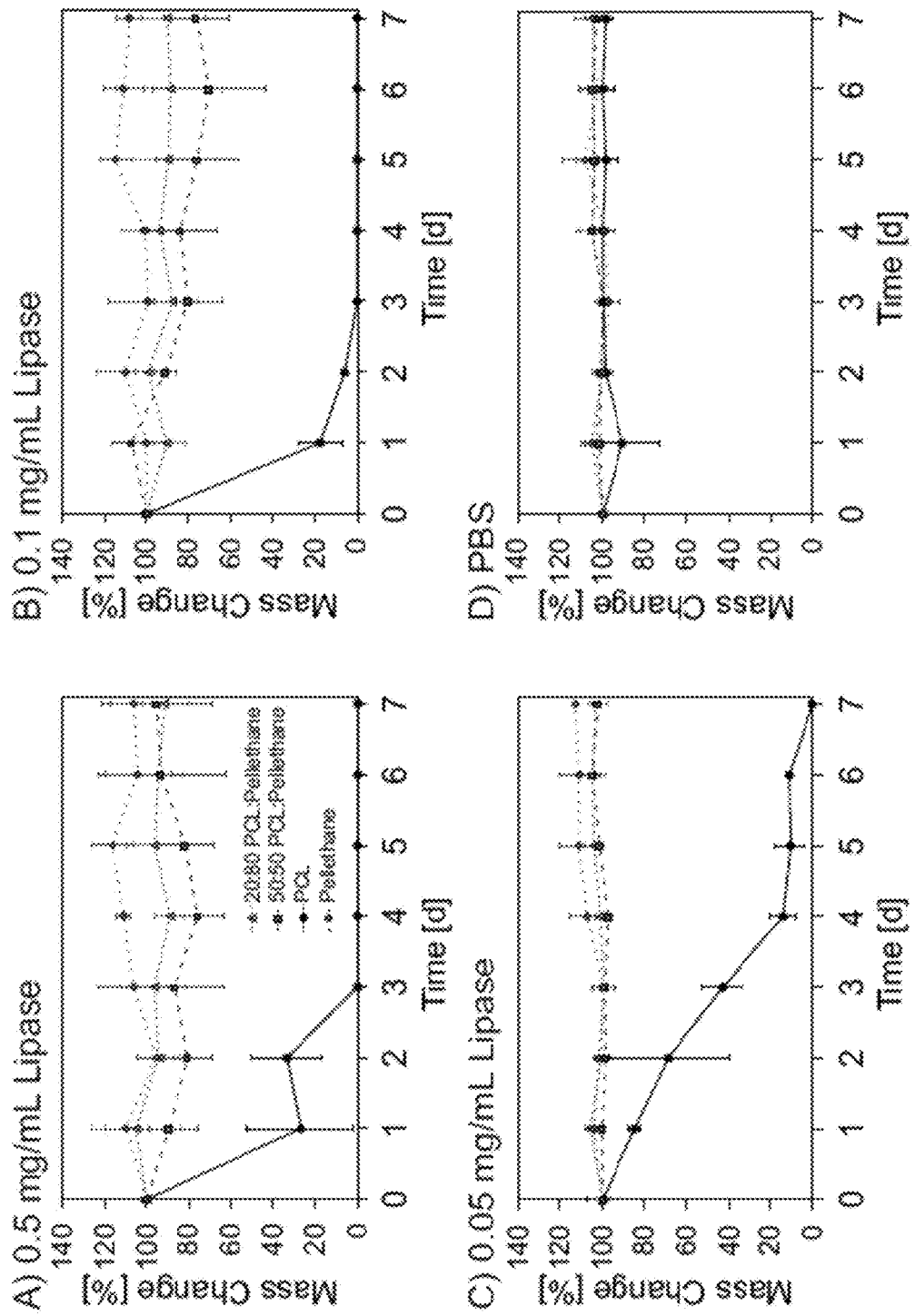
Figure 10:
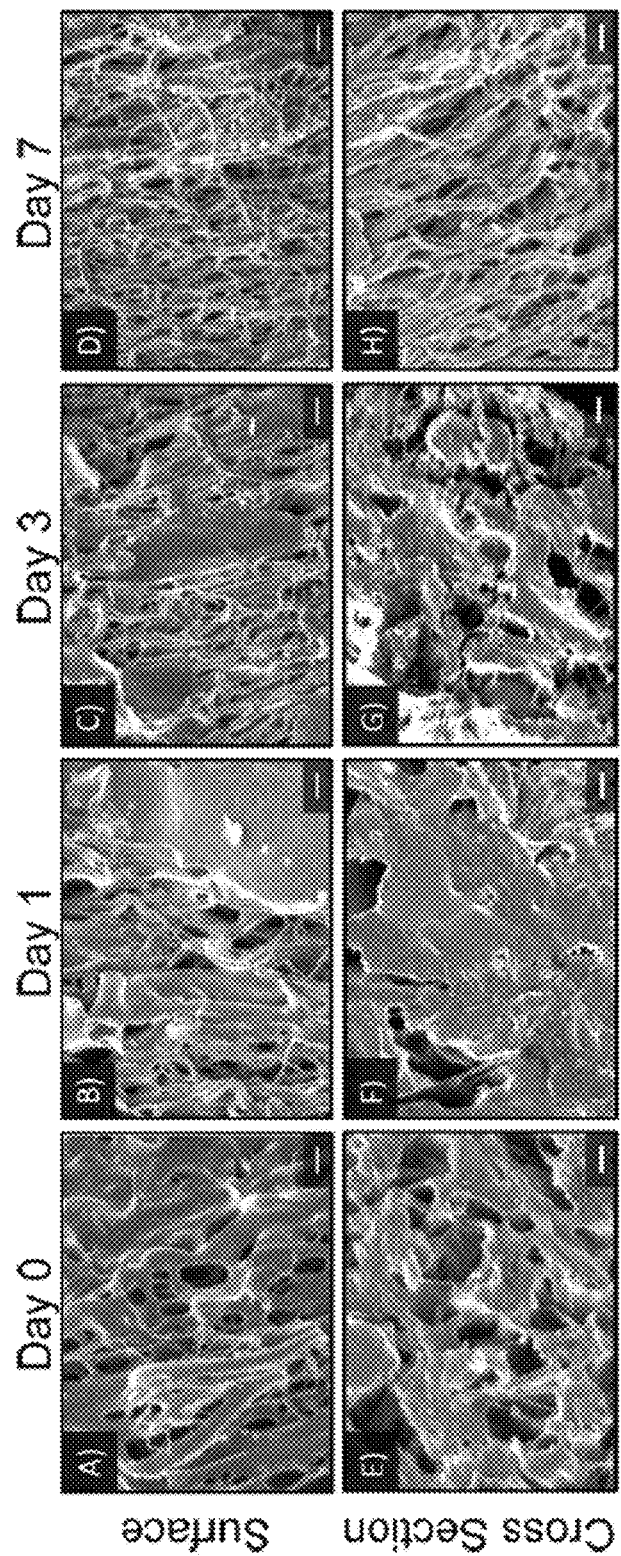
Figure 11:
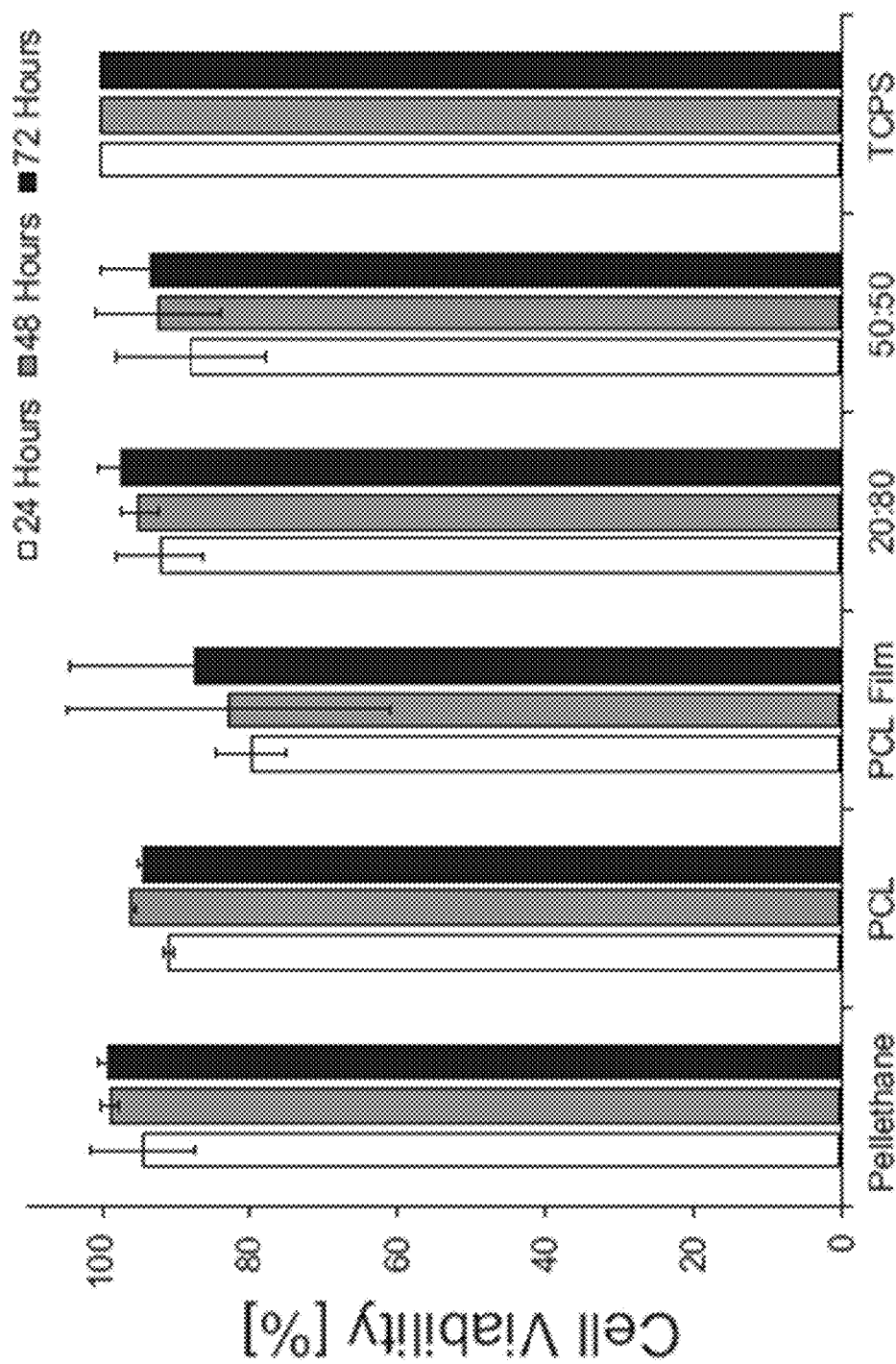
Figure 12:
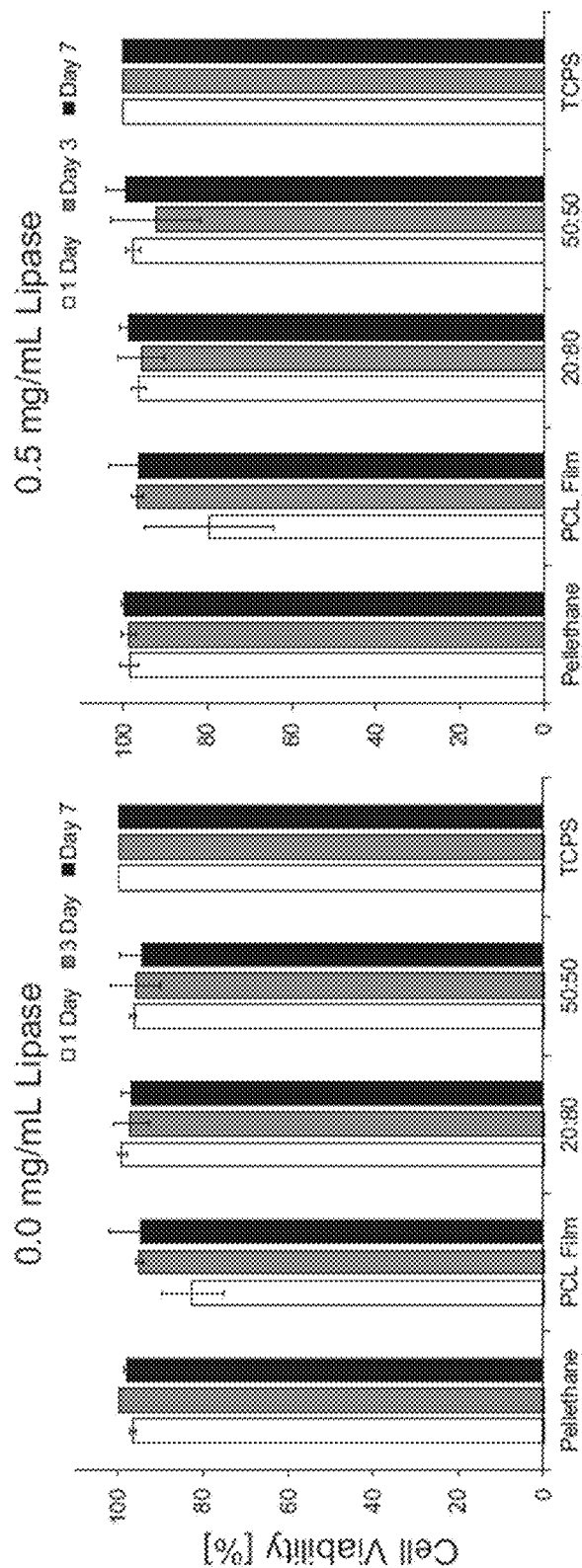

FIGS. 9A though 9D is a series of graphs showing mass change during degradation of exemplary compositions according to the present invention;

FIG. 10 is a series of scanning electron microscope (SEM) images of 50:50 PCL:PELLETHANE® incubated in 0.5 mg/mL of lipase according to the present invention;

FIG. 11 is a series of graphs of cell viability of C3H/10 T½ cells cultured directly on fiber composite and non-composite control samples in the absence of lipase; and FIG. 12 is a series of bar graphs of cell viability of C3H/10 T½ cells cultured directly on fiber composite and non-composite control samples in (left) a lipase-free control medium or (right) the presence of 0.5 mg/mL lipase.

DETAILED DESCRIPTION OF THE INVENTION

Figure 1:
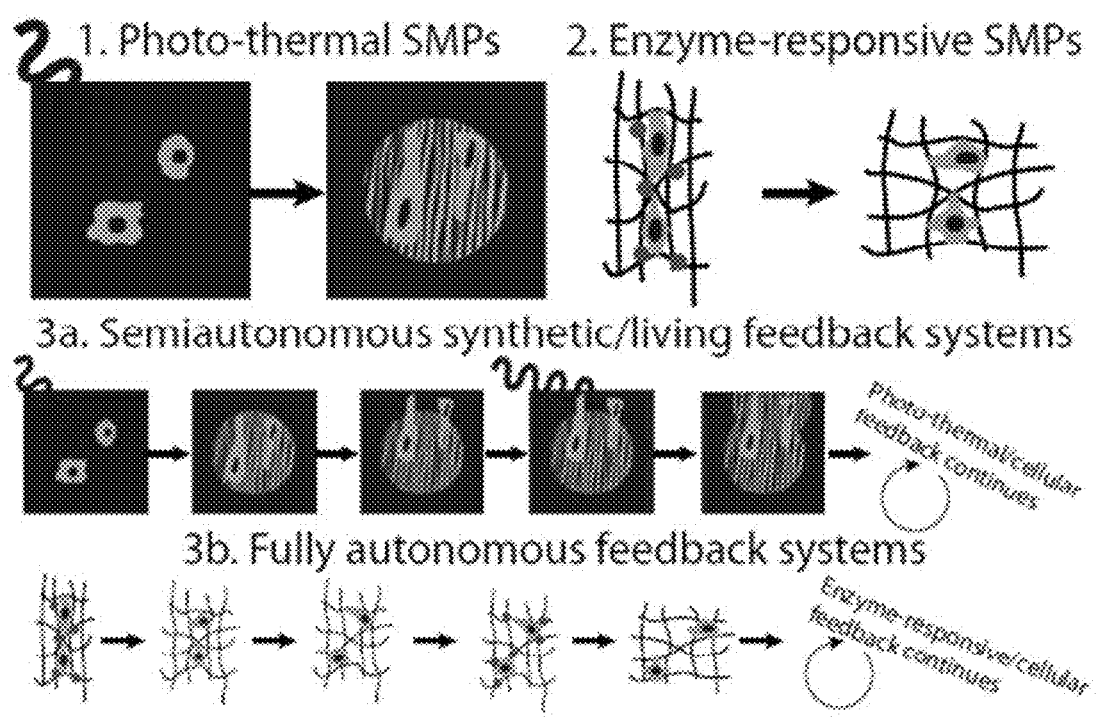

Referring to the figures, wherein like numeral refer to like parts throughout, there is seen in FIG. 1 an enzyme responsive shape memory polymer that may be used for a fully autonomous feedback system based on photo-thermal shape memory polymer uses. More specifically, the enzyme responsive shape memory polymer may comprise a glassy, cross-linked shape memory polymer that incorporates ester bonds responsive to the present of an enzyme. For example, PCL-based polyurethanes (featuring simple alternation of PCL diol and lysine-based diisocyanate) are degradable by Amano lipase PS. Such polyurethanes can be made in high molecular weight suitable for the preparation of fine fibers by electrospinning.

Figure 2:
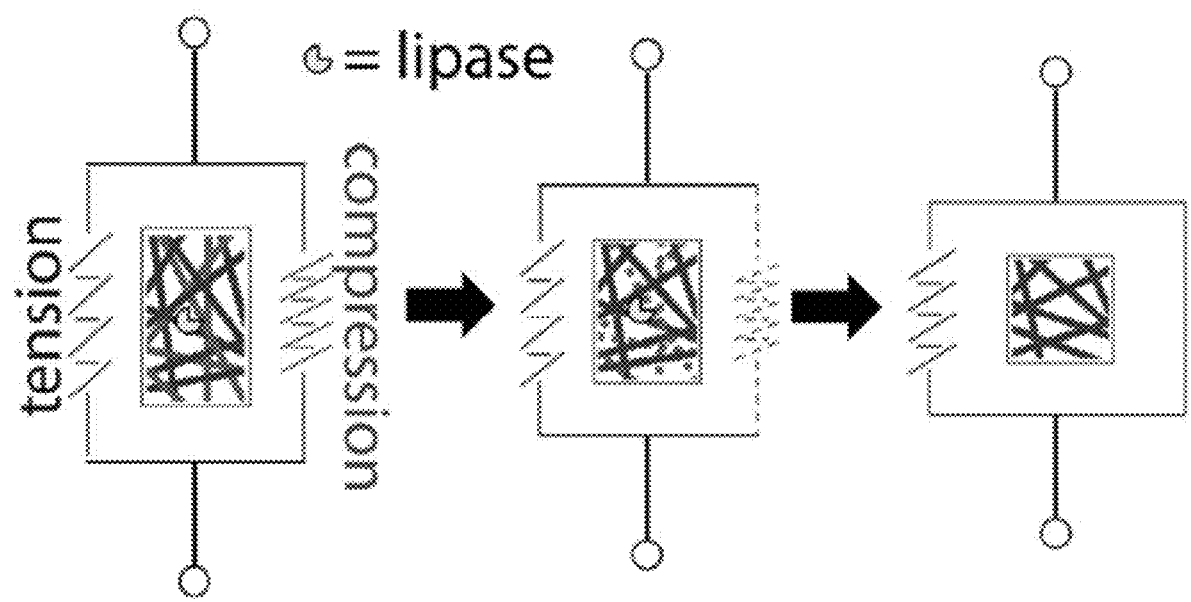

As porous shape memory polymer composites, wherein two polymer compositions are interwoven so that one serves the function of shape recovery and the other shape fixing (or "programming"), the present invention may involve thermos-mechanic postprocessing of the porous materials into a state wherein fibers are welded together, the elastomeric phase is in tension, and the fixing phase is in compression. Referring to FIG. 2, depending on composition, enzymatic degradation may then proceed on either: (i) the fixing phase, resulting in scaffold contraction or (ii) the recovery phase, resulting in scaffold expansion.

For the first approach, a non-degradable thermoplastic elastomer may be dual electrospun with a polycaprolactone based TPU. An electrospun interwoven scaffold may be stretched and heated to a temperature between the crystallization temperature of PCL (the as-spun PCL web will feature low crystallinity due to high molecular weight) and the hard-block melting point of the elastomer. Upon cooling and release of uniaxial or biaxial tension, the fixing phase will be compressed and the composite ready for enzymatically triggered contraction.

For the second approach, the elastomer may be a PCL copolymer-based polyurethane amorphous elastomer that is both degradable and elastomeric. This polymer will be dual electrospun with PVAc, a non-degradable polymer. Using the thermomechanical postprocessing described above, the PVAc web will be put into compression so that upon enzymatic degradation of the elastomeric phase the scaffold expands.

Enzymatically triggered contraction and expansion may involve exposure of the interwoven composite webs to Amano lipase PS using a DMA water immersion fixture in forcecontrol mode. Degradation may likely lead to contraction or expansion of the materials, quantified in relation to the relative percentages of recovery and fixing phases. Upon determination of the compositions maximizing the enzymatically induced shape change, the cellular release of lipase may be considered, particularly hepatic triglyceride lipase secreted from the human hepatoma cell line HepG2. For these studies, it is possible to chemically initiate enzyme secretion prior to or after cell seeding and proliferation by treatment with mevinolin, previously reported to double the release rate of lipase. A heterogeneity in strain (contractile or expansive) is expected in response to natural heterogeneity in cellular secretion of lipase. As mechanobiological cues may trigger lipase secretion, potentially non-linear or "biocatalytic" phenomenon may be unveiled. For example, a cascade of chemically initiated enzyme release and associated strain may be followed by mechanically initiated enzyme release that accelerates the process and localizes strain dramatically. If observed, the experiments may suggest nonlinear bio-chemo-mechanical systems ripe for modeling efforts.

Two forms of enzyme responsive shape-memory triggering may be studied: bulk triggering by administration of soluble enzyme; and localized triggering by cell-produced enzyme. In the first, thin (100 μm), nanofibrous, electropun mats, similar to those studied with thermally-triggered SMPs, may be studied without cells present. Cell-free samples may be used to analyze the samples in a one-way shape-memory cycle (1WSMC) in a DMA, with a systematic study of the relationship between soluble enzyme concentration and shape-memory recovery kinetics and magnitude. In the second set of studies, samples cultured with adherent HepG2 cells at 37° C. may be used to study localized triggering by cell-produced enzyme. For this study, localized shape-memory triggering of electropun fibers may be analyzed by time-lapse fluorescence microscopy, in which observation of cells and randomly distributed fluorescent silica nanobeads in the fiber mat (incorporated during spinning) may be used to quantify the zone of recovery, quantified by finding the average maximum radius from each cell at which particles are displaced by shape-memory recovery. The results of both sets of studies may be used to tailor cleavable ester bond density in pursuit of efficient triggering by bulk or by cell-produced enzyme.

For cytocompatibility testing, C3H/10T½ cells may be used. For localized triggering by cell-produced enzyme, HepG2 (ATCC) cells may be used.

Results from cytotoxicity assays may be used to modify the material chemistry, cleavable ester bond density, and/or bulk enzyme concentration protocol, if needed. For testing of material cytocompatibility in the absence of enzymatic triggering, the direct contact assay and Live/Dead assay will be performed with C3H/10T½. For testing of cytocompatibility during bulk enzymatic triggering, addition of medium not containing enzyme (non-toxic control) and medium containing phenol at a concentration of 64 g L-1 (toxic control) may be compared with the experimental groups, which may receive enzyme at the concentrations studied during characterization of shape-memory properties. For cytocompatibility during localized triggering, cytotoxicity will be assayed by direct observation of HepG2 morphology and by Live/Dead assay in experimental groups paralleling those used to characterize localized shape-memory triggering.

Once specific compositions are developed and characterized, synthetic/living feedback systems in which feedback between smart material and living cells drives individual, collective, and/or emergent behavior in both material and cells may be studied. To create a analytic model, photo-thermal SMPs may be employed in a semiautonomous closed-loop system in which real-time computational analysis of cell motility will be used to control photo-thermal shape-memory triggering, and vice versa. Real-time analysis of cell motility will be achieved through application of a cell-tracking algorithm. Localized photo-thermal triggering will be controlled by the cell-tracking algorithm and accomplished via a 470 nm LED light source coupled to the fluorescence microscope on which live-cell imaging is performed. This aspect will investigate what system in which spatial and temporal control of photo-thermal shape-memory triggering is guided by motility metrics derived from real-time computational analysis of cell motility, what phenomena, such as collective and emergent behaviors, are observed and do these phenomena exist in the absence of a synthetic/living feedback system. Successful completion of this objective is expected to open to inquiry a new area of research in which computational control of synthetic/living feedback systems enables exploration of phenomena related to interaction of the material and living cells or tissue.

The focus may be on a semiautonomous system in which it is possible to adjust the feedback relationship between cell behavior and material response, and vice versa, by modifying how calculated motility metrics are used to control photo-thermal triggering. A staged approach may be used, initially using an available polymer formulation and then shifting, in later stages, to the enzyme responsive shape memory polymer of the present invention.

The initial model may be developed using a glassy, crosslinked polymer formulation that has been used extensively in cytocompatible applications, tert-butyl acrylate (tBA) and butyl acrylate (BA). A copolymer composition of 95 wt % tBA and 5 wt % BA yields a Tg of 45° C. when dry, which is lowered to 40° C. when hydrated, due to water plasticization (Yang et al., 2013). Because this Tg is close to body temperature (37° C.) and of sufficient breadth to lead to shape-memory recovery at body temperature when under hydrated cell-culture conditions, cell experiments that employ this substrate will be conducted at 30° C. (rather than the 37° C. enabled by the materials to be developed in Objective 1), a mildly hypothermic temperature that is suitable for extended live-cell imaging and cell analysis. Work initiated with the tBA/BA system will shift to the enzyme responsive shape memory polymer of the present invention when that system is sufficiently characterized in terms of shape-memory properties, photo-thermal stimulation, and cytocompatibility.

Cell culture and imaging will be performed using the techniques described above. The photo-thermal protocols will be similar for either the tBA/BA system or the enzyme responsive shape memory polymer of the present invention, but with the former conducted at an ambient temperature of 30° C. and the latter at 37° C. For real-time analysis of cell motility, a contour-based tracking algorithm that has been developed and successfully employed in analysis of cells interacting with SMP substrates may be used. The adaptation will convert the algorithm from a post-imaging analysis to a real-time analysis run concurrently with live-cell imaging. To achieve this advance, which may result in a uniquely powerful algorithm for the study of cells interacting with smart materials, MATLAB's ability to interface directly with the microscope software, Micro-Manager, will be used. Both MATLAB and Micro-Manager operate through a Java based platform. By linking Micro-Manager's main application programming interface file into MATLAB's working class structure, the existing contour-based tracking algorithm can be modified through MATLAB script and function files to direct, obtain, and process live cell images in real-time. The tracking algorithm outputs several physics-based statistical metrics, including meansquared displacement, velocity autocorrelation, and asphericity. It is possible to systematically vary which calculated motility metrics are used to control photo-thermal triggering, thereby controlling the nature of the feedback system. The focus will be on the most basic metrics, such as cell position and velocity, before investigating more complex metrics, such as asphericity.

Localized photo-thermal triggering may be controlled by the cell-tracking algorithm, operating through the Micro-Manager software, and will be accomplished via a 470 nm LED light source coupled to the fluorescence microscope (Leica DMI 6000B) on which live-cell imaging is performed. Photo-thermal stimulation of regions of varying size will be studied, from the ~350 μm diameter afforded by the 40× objective to the ~2600 μm diameter of a 5× objective. To enable microscopy-based visualization of substrate deformation, fluorescent silica nanobeads will be incorporated into the substrates. Because of interest in investigating phenomena in synthetic/living feedback systems and in determining whether these phenomena are unique or exist in the absence of a synthetic/living feedback system, we will also study "control" systems in which (1) the PEM substrate is static or (2) shape-memory triggering is not guided by cell behavior (e.g., triggering occurs at a pre-determined time and location).

For quantitative analysis of material and cell behavior, it is possible to leverage the physics-based statistical metrics—including mean-squared displacement, velocity auto-correlation, and asphericity—that are incorporated in the contour-based tracking algorithm. These metrics will be determined for the fluorescent beads in the PEM substrates and for cell nuclei on both of the materials. Statistical comparison of metrics across experimental and control groups will be used to identify phenomena that are unique to the synthetic/living feedback system. Further, statistical correlation between patterns observed in the material behavior and patterns observed in the cell behavior will be sought, as a step toward gaining mechanistic understanding of the feedback and allowing future modeling thereof.

The present invention may also include the design and study of novel synthetic/living feedback systems. This aspect may employ enzyme-responsive SMPs in a fully autonomous closed-loop system in which cell-behavior (enzyme release) triggers shape-memory activation, and vice versa. This aspect will answer the question as to what extent can localized triggering of the shape memory effect by cell-produced (enzymatic) stimuli create fully autonomous synthetic/living feedback systems that are regulated by material properties alone.

This aspect may employ the enzyme-triggered system developed above and will employ the electrospun mats described above to prepare scaffolds. Cell culture and imaging will be as described above, but low cell densities will be included to facilitate localized recovery. Triggering by cell-produced enzyme will be as described above. For quantitative analysis of material and cell behavior, it is possible to leverage the physics-based statistical correlation between patterns as described above.

EXAMPLE

To achieve the present invention, an enzymatically degradable material, poly(ε-caprolactone) (PCL), may be combined with an elastomeric non-degradable material, PELLETHANE® (an aromatic polyether-based thermoplastic polyurethane available from Lubrizol Advanced Materials of Cleveland Ohio). In this example, PCL acts as a shape fixer to hold the temporary shape while the PELLETHANE® provides the memory component or the force to return to the original shape. Upon exposure to lipase, the PCL degrades, allowing the PELLETHANE® to return to its original configuration.

Materials

PCL, lipase derived from *Pseudomonas cepacian*, and dimethyl formide (DMF) were obtained from Sigma Aldrich. Chloroform and tetrahydrofuran (THF) were purchased from Fisher Scientific, and PELLETHANE® was purchased from Lubrizol. PCL electrospinning solutions were prepared by dissolving 2 g of PCL in 10 mL of an 8:2 volume ratio solution of chloroform and DMF. PELLETHANE® electrospinning solutions were prepared by dissolving 1 g of PELLETHANE® in 10 mL of a 6:4 volume ra-tio solution of THF and DMF. Enzymatically triggered SMPs were spun by dual spinning PCL and PELLETHANE® to create a blend of the two fiber webs. The composition of PCL to PELLETHANE® was varied by changing the syringe pump flow rates.

Material Characterization

All samples were thermally characterized using high-resolution thermogravimetric analysis and dynamic scanning calorimetry. The heat of crystallization of PCL was used to calculate the actual % composition of PCL in the fiber composites and compared to expected composition dictated during the spinning process. Samples were thermally cycled in a Q800 Dynamic Mechanical Analyzer (DMA) to assess thermal shape memory ability. Briefly, samples were heated above the melt transition of PCL, stretched to 100% strain and cooled back to 0° C. to fix in the temporary shape. The force was then lowered back to zero and samples were heated at a rate of 2° C./min to measure sample recovery. This thermal cycling was repeated for wet DMA experiments.

Enzyme Degradation Behavior

Enzymatic shape recovery was assessed using bulk degradation experiments. Dog bones (ASTM D63) were cut from pure PELLETHANE®, PCL, and fiber composites. All samples were heated to 70° C. in an isothermal oven and strained to 100% using a custom manual stretcher. Samples were then placed in a freezer to cool to −20° C. to fix the programmed strain into the sample. Samples were then incubated in a phosphate buffer solution (PBS) with lipase concentrations ranging from 0.05-1 mg/mL in a shaker table set to 37° C. Three samples were removed from solution every 24 h to measure enzymatically triggered shape recovery. Solutions were changed every two days to preserve lipase activity. Samples were photographed before programming, after programming, and once dried after degradation. Before and after degradation, samples were weighed to measure mass loss and imaged using a scanning electron micro-scope to assess fiber morphology. Wet DMA experiments were used to precisely measure both the kinetics and time of shape recovery as well as the force exerted by the PELLETHANE® upon shape recovery. Cell cytocompatibility was assessed using a LIVE/DEAD assay to both fiber composite material chemistry and to enzyme-triggered shape recovery using a C3H10T½ mouse fibroblast cell line.

Results

Figure 3:
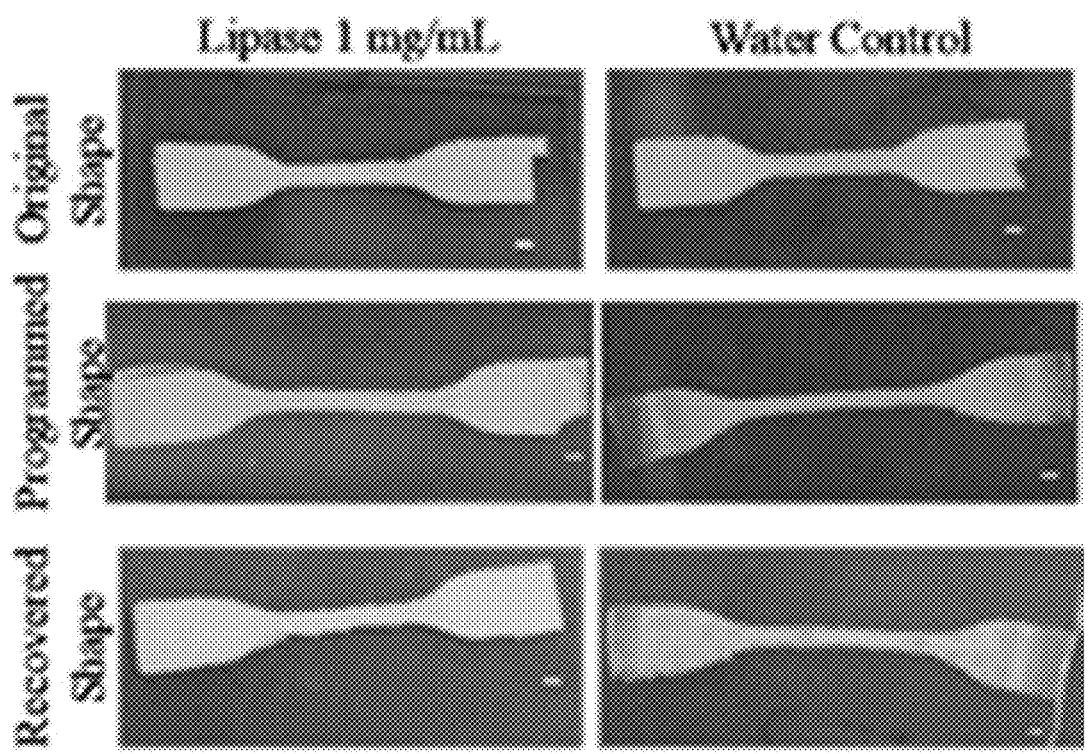

Thermal shape memory behavior was successfully demonstrated for fiber composites containing greater than 60% by weight PELLETHANE®. Bulk enzymatic degradation experiments successfully demonstrated enzymatically triggered shape recovery for all fiber composites, as seen in FIG. 3. After 24 hours the samples recovered from their programmed back to their original shape due to enzymatic activity. This was confirmed using a PBS control, which showed no shape recovery for this composition. PELLETHANE® controls showed no ability to fix a shape and no noticeable degradation, while PCL controls fixed a shape but were degraded within 24 hours making a recovery measurement impossible. Cytocompatibility assays were used to demonstrate the cytocompatibility of the fiber composites as well as the cytocompatibility of the enzymatic shape change. Submersion DMA was used to measure the force of the recovery and capture the precise time scale over which recovery occurs.

By enabling studies in which cells can trigger SMP recovery via enzyme release, this enzymatically triggered SMP is expected to make possible advances in cell mechanobiology. For example, the present invention provides a fully autonomous feedback system in which material behavior and cell behavior influence each other and a new understanding of structure-property relationships that span material to living (cellular) matter. The present invention may also provide and new insights into material-cell interactions relevant to materials intended for applications in contact with biological systems.

The present invention may be used for drug delivery vehicles that affect the target cells/organs through controlled release that is modulated by the physiological status of the cells/organs. The present invention may also be used as scaffolds that guide tissue regeneration through alterations in material and mechanical properties that are modulated by properties and behavior of the regenerating tissue. The present invention may additionally be used as platforms for stem cell culture that present a tailored microenvironment to maintain stem cell phenotype or, alternatively, to differentiate cells down a specific lineage in response to the phenotypic state of the cells. The present invention may further be used for decision-making ("sense and treat") biosensors that use feedback systems to control patient treatment. Thus, the uses of the present invention include fundamental advances in the field of biomaterials as well as breakthroughs in diverse bioengineering and healthcare fields.

Example 2

Figure 5:
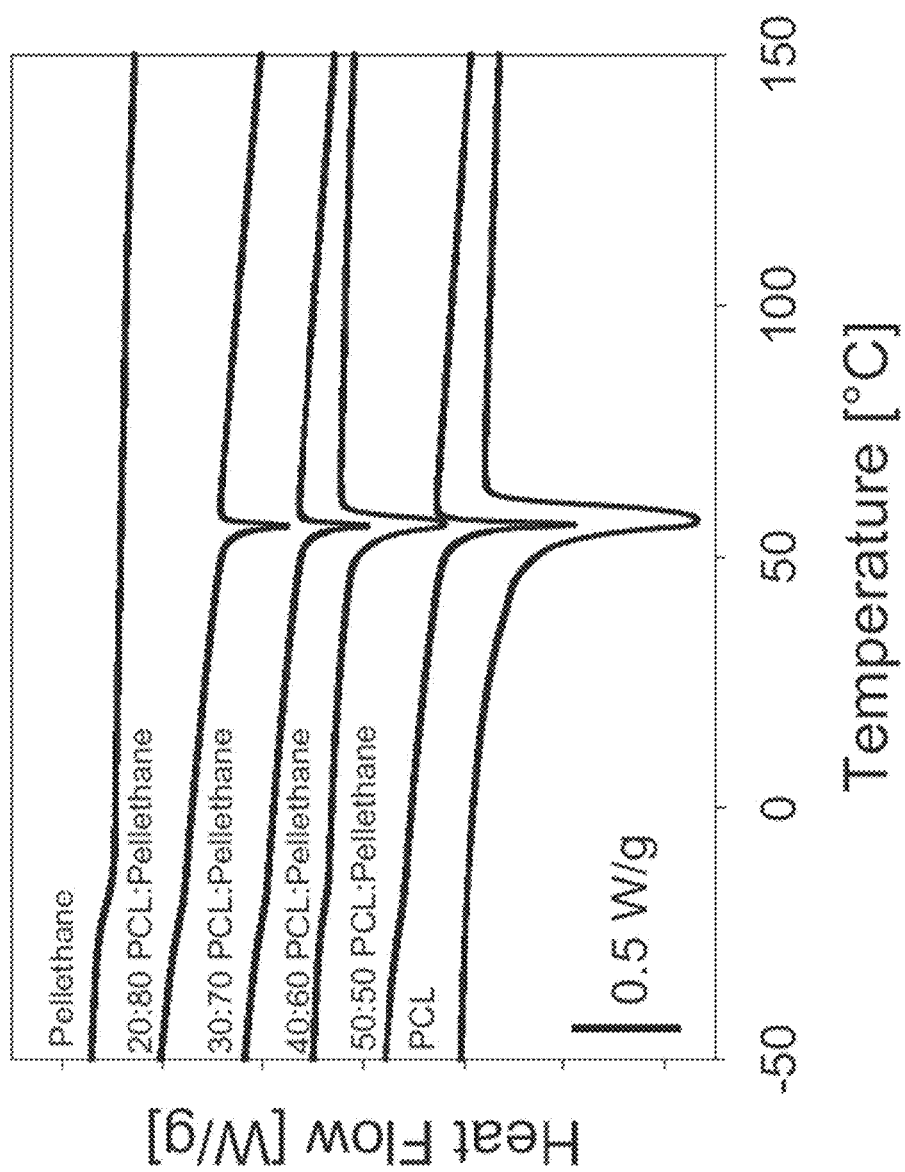
FIG. 5 is a series of differential scanning calorimetry (DSC) thermograms of all dual spun materials ordered in order of increasing poly(e-caprolactone) (PCL) content.

To develop an SMP that responds directly to enzymatic activity and can do so under cell culture conditions, an SMP that combines an enzymatically labile fixing component, poly(ε-caprolactone) (PCL), with an enzymatically stable elastomer, PELLETHANE® 5863-80A (hereafter, "PELLETHANE®"; a polyether-based thermoplastic polyurethane elastomer), was fabricated and characterized, as seen in FIG. 5. Fiber composites composed of poly(e-caprolactone) (PCL) (red) and PELLETHANE® (black) are heated and stretched above the $T_m$ of PCL to program the samples. The composites are then cooled to fix the temporary shape, putting the PELLETHANE® in an entropically unfavorable state. In this state, the PELLETHANE® applies a compressive force to the PCL, as the PELLETHANE® tries to recover back to its original shape but is resisted by the PCL crystallites that hold the temporary shape. Exposure to the enzyme lipase degrades the PCL portion of the fiber composite. As the PCL degrades, the force resisting the PELLETHANE® is gradually removed and the PELLETHANE® acts as an entropic spring to return back to its original conformation, recovering the permanent shape of the composite.

Thus, the two materials were selected so that, when heated above the $T_m$ of PCL and then stretched and subsequently cooled, a temporary shape in which the PCL is under compression and the PELLETHANE® under tension could be achieved. When later incubated in a solution of lipase— an enzyme produced by both eukaryotes and prokaryotes that hydrolyzes ester bonds in polyesters, the PCL would be degraded enyzmatically, allowing the PELLETHANE® to contract back to its original shape. Fabrication was performed via dual jet electrospinning. Samples of varying % PCL content, referred to collectively hereafter as "fiber composites," were prepared to study the dependence of enzymatic recovery on sample composition. Two non-composite controls were used: samples containing only PCL (a control both for achievable shape fixing and for complete degradation in enzyme); and samples containing only PELLETHANE® (a control both for lack of shape recovery and for lack of degradation in enzyme). Enzymatic shape recovery was studied using bulk degradation experiments in a lipase solution. Enzymatic recovery was quantitatively and qualitatively assessed via scanning electron microscopy (SEM), length measurements, and mass measurements. The cytocompatibility of the fiber composites and of the process of enzymatic recovery were assessed by respectively culturing of cells on samples without and with lipase present in the medium.

Materials

PELLETHANE®® (5863-80A) pellets were kindly supplied by the Lubrizol Corporation. Poly(s-caprolactone) (PCL) (Mn=80,000 g/-mol) pellets, chloroform ($CHCl_3$), N,N-dimethylformamide (DMF), and lipase derived from *Pseudomonas cepacia*, were purchased from Sigma-Aldrich. Tetrahydrofuran (THF) was purchased from VWR International. All materials were used as received. C3H/10 T½ cells (passage 8) were obtained from the American Type Culture Collection (ATCC) and expanded to passage 12-15 for experiments. Basal medium Eagle, fetal bovine serum, GlutaMAX, penicillin/streptomycin and LIVE/DEAD stain were all obtained from Invitrogen and used as received.

Fabrication

An 11 wt % electrospinning solution of PELLETHANE® was prepared by dissolving 11 g of PELLETHANE® in a 1:1.5 by volume solution of DMF:THF. A 15 wt % electrospinning solution of PCL was prepared by dissolving 15 g of PCL in a 1:4 by volume solution of DMF:$CHCl_3$. Solutions were stirred continuously for at least 24 h, at which time complete dissolution of the polymer was confirmed visually.

All samples were fabricated by dual electrospinning, in which two materials can be spun simultaneously to create a blended fiber mat (Schm. S1). Samples were electrospun using a custom electro-spinning apparatus composed of a rotating cylindrical drum collector (95.6 mm diameter, 300 mm width), SPRAYBASE® electro-spinning syringe pumps, and SPRAYBASE® voltage sources with a multihead emitter. Two solution emitters, one for the PELLETHANE® solution and one for the PCL solution, were used for this work. To vary the compositional ratio of the PCL to PELLETHANE® in fiber composites, the flow rate of PCL was set between 2.02 and 8.07 mL/h, while the PELLETHANE® flow rate was held constant at 11 mL/h, resulting in composites ranging from 20% to 50% PCL by mass. 22 G needles were attached to emitters and a voltage applied to the needle tip: 9-10.5 kV for the PCL, depending on the flow rate; and 12.5 kV for the PELLETHANE®. The needle tip to mandrel distance was held constant at 148 mm for both emitters. A negative voltage of −1000 V was applied to the mandrel to improve fiber deposition. A rotational speed of 2000 rpm was used to align the fibers during electrospinning. To ensure uniform fiber deposition, the emitter needle tips were translated across the width of the mandrel following a square wave velocity profile with a peak velocity of 100 mm/s.

Non-composite PCL and PELLETHANE® fiber mat controls were fabricated similarly, but using only one emitter. A flow rate of 8.07 mL/h with 10.5 kV was used for PCL and a flow rate of 11 mL/h with 12.5 kV was used for PELLETHANE®. All other spin conditions were held constant. For enzymatic recovery experiments, because the PCL fiber mats (containing no PELLETHANE®) were difficult to mechanically program, PCL controls were pressed in a hot press between two Teflon spacers at 70° C. to create a PCL film. In addition, the PCL present in fiber composites melts during heat treatment and during programming; the resultant PCL film morphology present in fiber composites is similar to the PCL films prepared for the enzymatic recovery experiments. For assessment of cytocompatibility of material prior to enzymatic recovery, non-composite PCL fiber mats were washed in hexane and then cut in half. A portion of each fiber mat was compression molded (as above), and cell culture samples were cut from both the fiber mat and the film. The cytocompatibility of both the PCL fiber and film morphologies was studied in the event that the mixed PCL fiber and film morphologies present in fiber composites differentially affected cells. For assessment of cytocompatibility of material during enzymatic shape recovery, of the PCL fiber and film samples, only the PCL film samples were studied, due to the difficulty in mechanically programming PCL fiber mats.

Thermal analysis was performed to measure the thermal degradation of the materials and to ensure that only fiber composites that had calculated composition values close to the prescribed values were used in subsequent experiments. Following thermal analysis, samples were heat treated, by heating the samples to 70° C., to allow any residual strain programmed during the electrospinning process to recover. Heat treatment was performed before dynamic mechanical analysis, shape memory testing, and enzymatic degradation experiments. For cytocompatibility experiments, samples were washed with hexane, to remove any residual toxic solvents that may have remained from electro-spinning of the samples, and were then heat treated.

Thermal Analysis

Thermal gravimetric analysis (TGA) (TA Instruments Q500) was performed on all fiber samples to measure the thermal degradation of the materials. To allow high-resolution analysis of thermal degradation events, the analysis employed a protocol in which samples are run at a variable heating rate that decreases as detected mass loss rate increases (TA Instruments Dynamic Rate Hi-Reslm Ramp). Briefly, and following methods reported in the field, samples were heated at a maximum rate of 50° C./min to 600° C. with a resolution of 4° C. and a sensitivity (instrument specific) of 1. When the instrument detected a thermal degradation, the heating rate automatically decreased (below 50° C./min) to capture fully the degradation event, before continuing with the test.

Differential scanning calorimetry (DSC) (TA Instruments Q200) was performed on all samples using a DSC equipped with a refrigerated cooling system to record thermal transitions. For each test, samples weighing 3-5 mg were loaded into a T-zero aluminum plan and equilibrated by cooling to −60° C. Samples were then heated at 10° C./min to 170° C. and then immediately cooled at 5° C./min to −50° C. This initial heating and cooling cycle was used to erase any thermal history. Samples were then heated at 10° C./min to 170° C. to measure the glass transition ($T_g$) and melting transition ($T_m$) of the fiber mats. The composition of each sample was calculated using the heat of crystallization of the PCL via Equation (1). This equation assumes that the degree of crystallinity of the PCL phase is the same in all samples, which is reasonable because PCL readily crystallizes at room temperature. Calculated values were compared to predicted values prescribed by the flow rate of the PCL during electrospinning. Only fiber composites that had calculated composition values close to the prescribed values were used in subsequent experiments.

$$W_{PCL}(\%) = \frac{\Delta H_{PCL-COMP}}{\Delta H_{PCL-pure}} * 100 \quad (1)$$

Dynamic mechanical analysis (DMA) was used to measure the temperature dependences of the tensile storage modulus for all materials, as the temperature dependence of the storage modulus is a strong predictor of shape memory ability. Dog bones (ASTM D638 type IV, scaled down by a factor of 4) with a gauge length of 6.25 mm and width of 1.5 mm, were cut from fiber mats. Samples were then loaded into a DMA TA Q800, cooled to −70° C., and then heated to 200° C. at a 2° C./min while applying a small tensile deformation at a frequency of 1 Hz.

Shape Memory Ability

Thermal (not enzymatic) shape memory cycles were performed on a DMA (TA Instruments Q800) operated in controlled-force mode to quantify the shape memory ability of the fiber composites. Briefly, each sample was first heated to 60° C. (above the $T_m$ of PCL) and loaded at 0.03 N/min until 100% strain was reached. Samples were then cooled at 2° C./min to 0° C. and the load released at 0.1 N/min. To complete the cycle, samples were then heated at 2° C./min and the shape recovery recorded. This full cycle was repeated three times. The fixing ($R_f$) and recovery ($R_r$) ratios for each recovery event were then calculated using Equations (2) and (3), where shape "x" refers to the shape or deformation being programmed into the sample in the current cycle and shape "y" is the shape or deformation after the previous cycle $$Rf(x) = \frac{\varepsilon x}{\varepsilon x, \text{load}} \quad (2)$$

$$Rr(x \to y) = \frac{\varepsilon x - \varepsilon y, rec}{\varepsilon x - \varepsilon y} \quad (3)$$

In Eq. (2), $\varepsilon_x$ and $\varepsilon_{x,load}$ are, respectively, the strains measured after cooling and unloading (thus, the strain fixed) and before unloading (or the attempted programmed strain). $\varepsilon_{y,rec}$ is the strain achieved after recovery for shape y, and $\varepsilon_y$ is the strain before programming shape y.

Enzymatic Shape Recovery Experiments

Enzymatic shape recovery was assessed using bulk enzymatic degradation studies under simulated cell culture conditions. Samples were cut using a dog bone punch (the same punch used for DMA shape memory cycling), then heated and stretched to 100% strain using a custom screw-driven manual stretcher. With samples so stretched but still in the stretching device, the stretcher and sample were transferred to a freezer at −20° C. to quickly fix the temporary shape (note: such fixing was stable at room temperature). Samples were photographed before and after mechanical programming (stretching and fixing) for subsequent use in image-based calculation of programmed strain and of strain during enzymatic shape recovery. Samples were then weighed and incubated in PBS solutions containing 0, 0.05, 0.1, or 0.5 mg/mL of lipase. The enzyme concentration range of 0.5-0.05 mg/mL was selected based on a previous experimental and kinetic modeling evaluation of lipase activity with respect to concentration for degradation experiments and was chosen such that the highest enzyme concentration would ensure degradation of the PCL in a relatively short time frame (i.e., days) while the lower concentrations would reflect more physiological enzyme concentrations, though it is difficult to correlate in vitro concentration to activity in vivo. Experiments were conducted over 7 d, with one sample collected for analysis every 24 h. Experiments were repeated 3 times using fiber mats independently prepared (electrospun) on different days. Upon collection, the samples were washed using deionized water, dried in a desiccator for 24 h, and then transferred to a vacuum oven at 40° C. for 48 h to ensure full drying of the samples. Samples were then photographed and weighed. Mass loss was calculated using Eq. (4):

$$Mr(\%) = \frac{M(t)}{Mo} * 100 \quad (4)$$

where $M_r$ is the % mass remaining, M(t) is the measured mass after degradation, and $M_o$ is the original mass of the sample. To calculate programmed strain and strain during enzymatic shape recovery, images of samples before programming, after programming, and after sample collection were analyzed in ImageJ 1.51j8 (National Institutes of Health, Bethesda, Md., USA). In each image, a linear measurement of the gauge length was made along both sides of the dog bone samples. The two measurements were averaged. The measurements were performed independently by three separate users and averaged across all users. The change in strain (ε) over the course of enzymatic strain recovery for each sample was calculated using Eq. (5):

$$\Delta \varepsilon (\%) = \frac{(l_o - l_s)}{l_o} * 100 \quad (5)$$

where $l_o$ is the measured gauge length for the original, pre-strained sample and $l_s$ is either the measured gauge length for the strained sample immediately after programming or after collection. DSC experiments were used to assess the PCL crystallinity before and after degradation. Samples were run hydrated immediately post degradation to better capture the crystallinity of PCL at the point of sample recovery.

SEM Imaging

Fiber mats were imaged using SEM (JEOL 5600) to assess changes in fiber morphology during enzymatic shape recovery experiments and, additionally, to ensure that fiber morphologies were similar between fiber composite batches. Samples of fiber mats were collected for SEM immediately after electrospinning, immediately after the heat treatment used to recover residual strain programmed during the electrospinning process, and after days 0 through 7 of the enzymatic shape recovery experiments. All samples were mounted on a metal plate and sputter coated for 45 seconds (Denton Vacuum-Desk II). Samples were imaged with an accelerating voltage of 10 kV and a spot size of 36.

Cell Selection and Expansion Culture

All cell experiments were performed with the C3H/10 T½ mouse embryonic fibroblast line, a cell line we have frequently used in the development and application of cytocompatible SMPs. Cells were obtained from the ATCC at passage 8, and cells of passage number 12-15 where used for experiments, following the recommendations of the ATCC. Cells were cultured in basal medium Eagle with 10% fetal bovine serum, 1% GlutaMAX, and 1% penicillin/streptomycin and passaged once 70-80% confluence was reached.

Cytocompatibility of Material Prior to Enzymatic Shape Recovery

Cells were directly cultured on samples to assess material cyto-compatibility. Fiber and film PCL samples were sterilized using UV light for 10 h, flipped over, and sterilized using UV for an additional 10 h. All materials were soaked in complete medium overnight to allow proteins to adsorb throughout the samples and then C3H/10 T½ cells were solution seeded onto the materials at 10,000 cells/cm'. Cell-seeded materials were then washed and stained with LIVE/DEAD at 24, 48, and 72 h time points with tissue culture polystyrene (TCPS) well plates acting as live controls for counting and analysis. Cell viability was calculated by dividing the total number of cells by the total number of live cells.

Cytocompatibility of Material During Enzymatic Shape Recovery

The cytocompatibility of enzymatic shape triggering was assessed by culturing cells on samples as the samples were incubated in lipase-containing medium over a one-week period. Samples were washed and sterilized as described in Section 2.8.2. Cells were seeded onto the samples at 5000 cells/cm' and allowed to attach for 3 h. The culture medium was then replaced with medium containing 0.5 mg/mL lipase, the highest lipase concentration used for shape recovery experiments. The lipase-containing medium was sterilized via filtration with a 0.45 gm filter prior to use. The non-toxic control was lipase-free medium. Media were changed every 2 days to mimic conditions used in the bulk degradation experiments. Samples were collected and cells stained with LIVE/DEAD stain at 1, 3, and 7 day time-points to assess cell viability. Cell viability was calculated as above (Section 2.8.2).

Statistical Methods

For numerical graphs, error bars show the sample standard deviation. Statistical analysis was performed using RStudio Version 1.1.453 (The R Foundation for Statistical Computing) and comparisons were made using a multiple comparison Holm t test. Significance was set at P<0.05. For enzymatic shape recovery (Section 3.3), PCL samples were excluded from comparisons as samples at some time points were completely degraded.

Results

Thermal Analysis

As anticipated, thermal transitions quantified by TGA, DSC (FIG. 5), and DMA showed that both PCL and PELLETHANE® were present in fiber composites and existed as separate phases, as evidenced by the separate transitions recorded in thermal analysis. TGA analysis showed that all fiber mats were dry before processing. PCL showed a single sharp degradation event, while PELLETHANE® showed a two-step degradation event. Fiber composites likewise showed a two-step degradation; however, the degradation of the PCL was occluded by the degradation of the PELLETHANE®, making TGA analysis of the two weight % s difficult. As a result, DSC was used to analyze the % content of the fiber mats. For the analyzed temperature range, PELLETHANE® controls demonstrated only a $T_g$, at approximately −20° C., while PCL controls showed only a $T_m$, at approximately 56° C. To ensure consistency across experimental runs, only fiber composites that came within a ±5% predicted PCL content were used for subsequent experiments. Analysis of post-heat treatment samples confirmed that the thermal transitions quantified by TGA and DSC were unaffected by the heat treatment used to recover residual strain programmed during the electrospinning process (data not shown).

DMA showed three well-separated thermal-mechanical transitions at approximately −20° C., 56° C., and 160° C. for the $T_g$ of the PELLETHANE®, the $T_m$ of the PCL, and the $T_m$ of the PELLETHANE®, respectively. For the approach of the present invention to achieving enzymatic shape memory, the ideal point for shape memory behavior would be above the $T_g$ of PELLETHANE®, so the material is within its elastic region, with the $T_m$ of PCL acting as the triggering temperature.

Shape Memory Ability

Figures 6A, 6B, 6C:
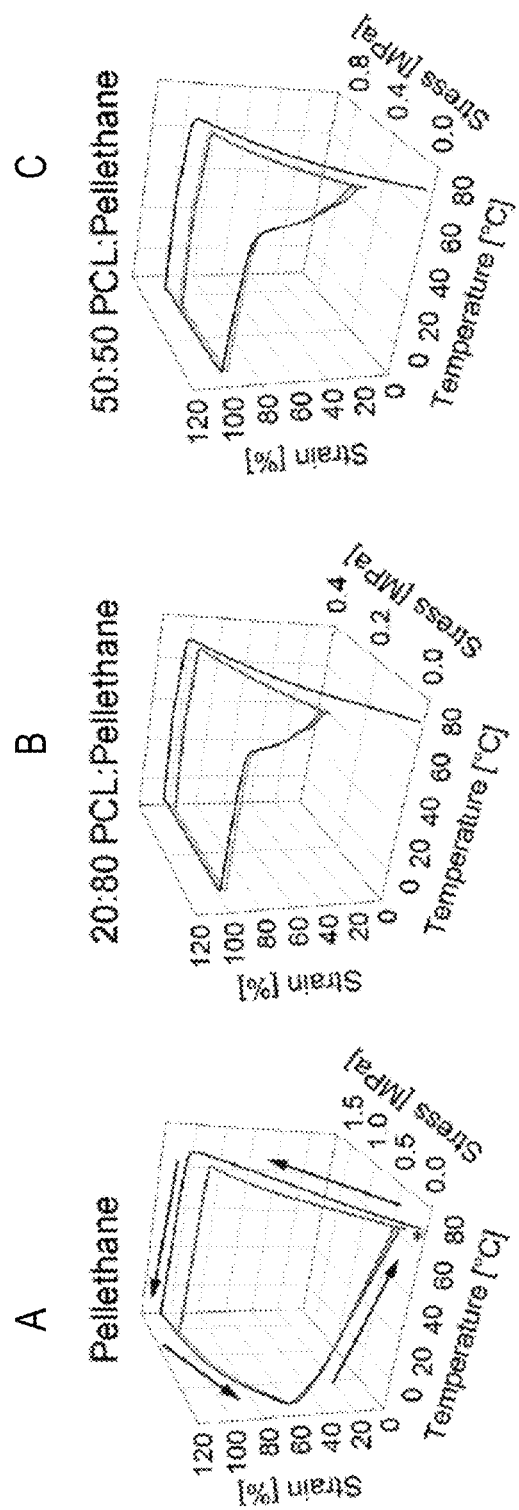
FIG. 6A through 6C are a series of thermal shape memory cycles showing (A) Pure PELLETHANE® has a fixing ratio ($R_f$) of 54% and a recovery ratio ($R_r$) of 87%; (B) 20:80 PCL:PELLETHANE® fiber composite has an $R_f$ of 93.5% and an $R_r$ of 85.1%; and (C) 50:50 PCL:PELLETHANE® fiber has an $R_f$ of 97.5% and an $R_r$ of 83.2%.

Thermal shape memory cycles demonstrated that strong shape fixing and recovery were achieved for fiber composite samples, as seen in FIG. 6. The PCL control yielded during the first stretch of the first cycle and was not included in analysis. The PELLETHANE® control seen in FIG. 6A showed a poor fixing ratio of 53%, indicating a low ability to fix a shape, and demonstrated a recovery ratio of 89%. For comparison, an ideal rubber features no (0%) fixing and complete (100%) recovery. The high recovery ratio for the PELLETHANE® control is attributed to the elasticity of the PELLETHANE® fibers, which is the driving force for shape recovery. This recovery ratio indicates that some strain is lost during mechanical cycling, which may be attributed to minor plastic deformation that occurs during the first thermo-mechanical cycle. The fixing ratio of fiber composites was 89% and 96% for the 20:80 and 50:50 PCL:PELLETHANE®, respectively, as seen in FIGS. 6B and 6C, indicating that increasing the PCL content increased the fixing ability of the fibers. The recovery ratio showed weak dependence on composition, with values of 89% and 84% for the 20:80 and 50:50 PCL:PELLETHANE®, respectively, as seen in FIGS. 6B and 6C. The 30:70 and 40:60 PCL:PELLETHANE® compositions showed similar results, with an increase in PCL content increasing the fixing ability of the fibers and the recovery ratio showing weak dependence on composition. All samples showed a diminished recovery ratio for the first cycle, which we attribute to minor plastic deformation of the PELLETHANE® fibers, as indicated by the strain in the samples not returning fully to zero. After a single mechanical conditioning step, the recovery of the materials increased. In light of the modest differences in shape memory ability observed across the four fiber composite compositions tested, only the two most extreme compositions, 20:80 and 50:50 PCL: PELLETHANE®, were studied in the ensuing enzymatic shape recovery and cytocompatibility experiments.

Enzymatic Shape Recovery

Figure 7:
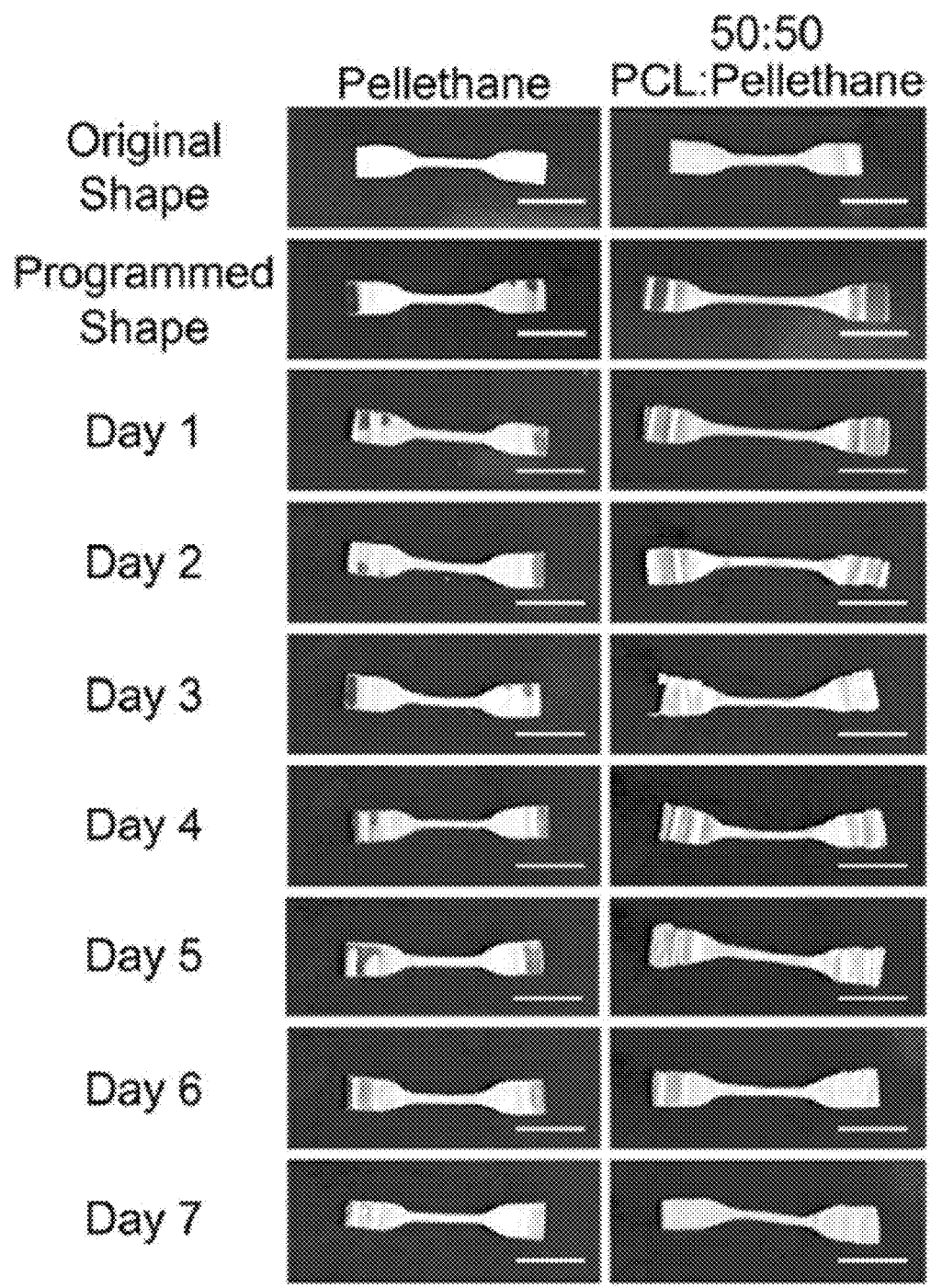
FIG. 7 is a series of images showing a macroscopic view of enzymatic recovery.
Figures 8A, 8B, 8C, 8D:
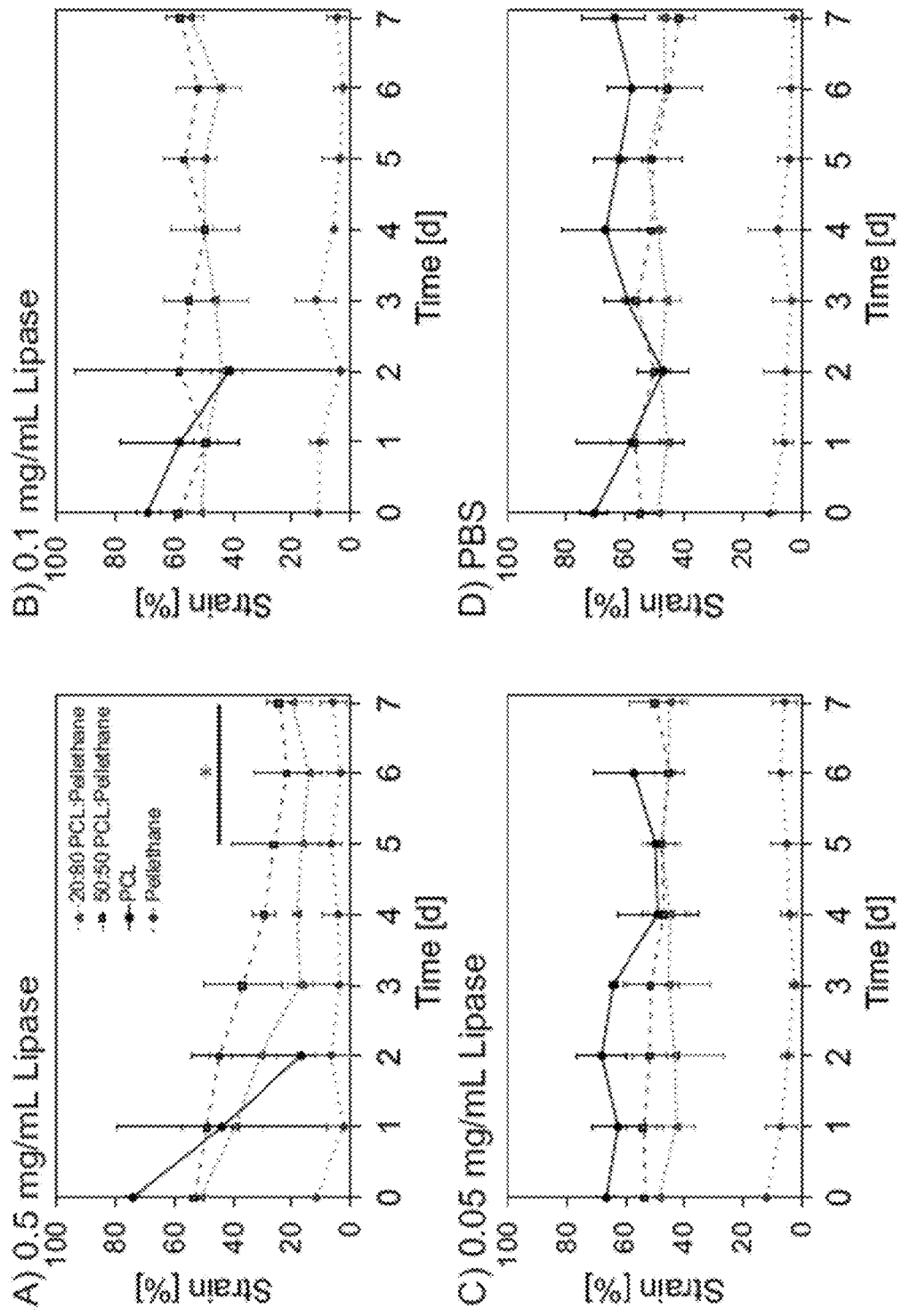
FIGS. 8A through 8D is a series of graphs of enzyme-triggered shape recovery of exemplary compositions according to the present invention over 7 days.

Enzyme-triggered shape recovery was observed in fiber composites (50:50 and 20:80 PCL:PELLETHANE@, as seen in FIGS. 7 and 8, as evidenced by decreasing strain over the 7-day experiment. However, shape recovery was only evident for the highest enzyme concentration studied (0.5 mg/mL). PELLETHANE® showed no measurable changes in strain for all conditions, as expected, while the fiber composites decreased in length over time, as seen in FIG. 8A. Lower concentrations of lipase degraded the PCL film control samples but did not trigger shape recovery in the fiber composites, as seen in FIGS. 8B and 8C. For fiber composites, sample lengths (and associated strains) in 0.5 mg/mL lipase solutions, as seen in FIG. 8A, remained significantly greater ($P<0.05$) than the PELLETHANE® controls until day 5, after which no statistical difference in length was observed, consistent with samples having recovered to the preferred length of the PELLETHANE®. In contrast, when incubated in 0.1 and 0.05 mg/mL (FIG. 8C) lipase, as seen in FIGS. 8B and 8C respectively, fiber composite sample lengths remained significantly greater than that of the PELLETHANE® controls at all time-points ($P<0.05$), consistent with fiber composite samples having not recovered. Further, PBS controls showed no measurable recovery for all groups, as anticipated, as seen in FIG. 8D. In particular, those samples incubated in only PBS exhibited no measurable change in strain with time, remaining strained at the magnitude programmed, which was significantly greater than that of PELLETHANE® control (incapable of strain-fixing), for all time points ($P<0.05$). PCL control samples were not included in statistical comparisons, as samples degraded significantly for all enzyme concentrations, including day 1.

Mass change measurements revealed significant mass loss for the PCL film, with rate of degradation increasing with increasing lipase concentration, while all other samples exhibited no measurable mass loss, as seen in FIG. 9. Control samples immersed in PBS showed no measurable mass change for any of the samples, as seen in FIG. 9D, indicating that mass loss was driven by enzymatic degradation instead of much slower hydrolytic degradation, as expected. The lack of observed mass change in fiber composites, as seen in FIG. 9, suggests that the observed strain recovery, as seen in FIG. 8, occurs primarily through reduction of PCL molecular weight, or disruption of the percolation of the PCL phase, not through loss of PCL mass. This finding is supported by the observed decrease in PCL crystallinity as samples are degraded. Upon exposure to lipase the PCL crystalline peak diminishes supporting the degradation disrupting the PCL crystallinity and thereby allowing the PELLETHANE® to recover.

Morphological analysis by SEM of samples undergoing degradation during exposure to enzyme revealed changes in sample morphology indicative of PCL degradation. Surface analysis of morphological changes in the 50:50 PCL:PELLETHANE® fiber composite incubated in 0.5 mg/mL lipase, as seen in FIG. 10, showed an initial (pre-degradation) morphology of fibers with a film or binder at the surface, as seen in FIG. 10A. Over the course of the degradation experiment, the morphology of the fiber composite transitioned from a mixed film-fiber morphology, as seen in FIG. 10A through 10C, to a predominantly fiber morphology, as seen in FIG. 10D, as PCL degraded, leaving behind primarily PELLETHANE® fibers. Analysis of cross-sections of 50:50 PCL:PELLETHANE® samples, as seen in FIG. 10E, showed an initial semi-continuous network of PELLETHANE® fibers interpenetrated incompletely by PCL binder, with significant porosity evident. As enzymatic degradation progressed over 7 days, the PCL binder increasingly degraded until, at day 7, as seen in FIG. 10H, the fraction of PCL had diminished substantially. The 20:80 PCL:PELLETHANE® samples showed similar morphological changes when incubated in 0.5 mg/mL lipase and both fiber composites (20:80 and 50:50) also showed similar morphological changes when incubated in the lower, 0.1 mg/mL, lipase concentration. In contrast, fiber composites incubated in 0.05 mg/mL lipase retained a mixed film-fiber morphology. The PELLETHANE® control showed no morphological changes, regardless of enzyme concentration. All fiber composites and controls showed no morphological changes when incubated in PBS.

Cytocompatiblity of Materials Prior to Enzymatic Shape Recovery

When mouse fibroblasts were cultured directly on fiber composites and non-composite controls in the absence of lipase, no statistically significant differences in viability were found, as seen in FIG. 11. Moreover, all groups had a viability of 75% or greater at all time-points. The PELLETHANE® control, PCL control, and fiber composites showed an average viability not statistically different from the TCPS control, indicative of cytocompatibility. Qualitatively, cells cultured on the 50:50 PCL:PELLETHANE® fibrous composite showed a random orientation that contrasted with that of cells cultured on the PELLETHANE® control, which showed an oriented morphology. This difference is likely due to the morphology of the PCL, which acts as a film (binder) in the fiber composites, as seen in FIG. 11, a morphological feature that does not exist between the aligned fibers of the PELLETHANE® control. Image analysis revealed a significantly higher number of cells on TCPS compared to all material groups, likely due to cells attaching to the bottom of the well (rather than the sample) during the seeding of material groups.

Cytocompatibility of Material During Enzymatic Shape Recovery

When mouse fibroblasts were cultured on fiber composites and non-composite controls incubated with 0.5 mg/mL of lipase or a lipase-free control medium, as seen in FIG. 12, no statistical differences in viability were found. Moreover, all groups had a viability of 75% or greater at all time-points. The PELLETHANE® control, PCL control, and fiber composites showed an average viability not statistically different from the TCPS control, indicative of cytocompatibility. As had been observed in the study of cytocompatibility prior to enzymatic shape recovery, as seen in FIG. 12, in the presence of lipase the PELLETHANE® control, PCL control, and fiber composites showed an average viability not statistically different from the TCPS control, indicative of the enzymatic degradation of PCL and, therefore, the phenomenon of enzymatic shape recovery being cytocompatible, as seen in FIG. 12. Image analysis again revealed a significantly higher number of cells on TCPS compared to all material groups, which is again likely due to cells attaching to the bottom of the well (rather than the sample) during the seeding of material groups.

DISCUSSION

The present invention thus comprises a new SMP design that responds directly to enzymatic activity to allow isothermal shape change, demonstrated as contraction of tensile specimens, under cell culture conditions. Electrospun fiber composites prepared using this design showed good thermal shape memory ability, with a PCL component acting as a shape fixer and a PELLETHANE® component acting as the memory component. When cultured in a 0.5 mg/mL lipase solution, programmed fiber composites showed enzymatic shape recovery within a 7-day test period. Cells cultured on enzymatic SMPs with or without 0.5 mg/mL lipase showed viability comparable to non-toxic controls, indicating that both the enzymatically-responsive SMP materials and the process of enzymatic shape recovery are cytocompatible.

Figure 4:
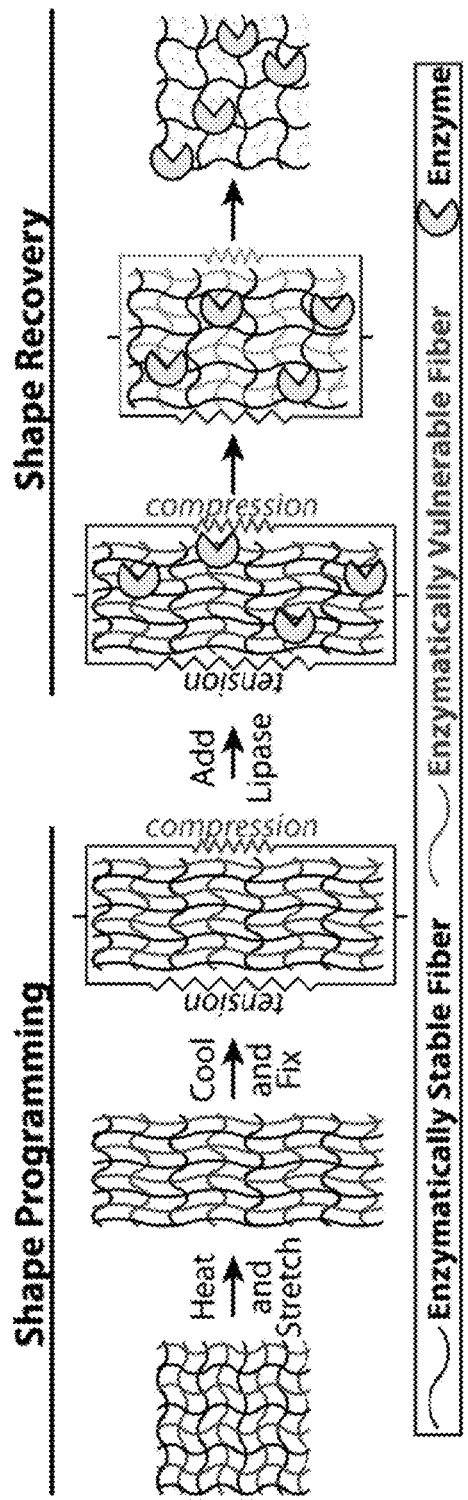
FIG. 4 is a schematic of the strategy used to achieve enzymatic shape memory fiber composites according to the present invention.

The enzymatic shape recovery achieved in the present work is dependent on enzyme concentration. Only samples incubated in the highest enzyme concentration, 0.5 mg/mL lipase, showed complete shape recovery, while samples incubated in lower enzyme concentrations and in a lipase-free control showed no measurable recovery. This enzyme concentration sensitivity is consistent with the strategy used to achieve enzymatic recovery, as seen in FIG. 4), wherein shape recovery is enabled by the degradation of an enzymatically labile fixing component and is only achieved when that component has degraded sufficiently. It is expected that, if degradation experiments were lengthened, all fiber composites would eventually show full strain recovery for all enzyme conditions studied.

The enzymatic SMPs did not demonstrate mass loss during recovery. This finding suggests that the mechanism of enzyme shape recovery is either a decrease in PCL molecular weight or de-percolation of the fixing phase. As either of these processes continue, the force exerted by the PELLETHANE® is able to overcome the force exerted by the PCL, leading to recovery back to the sample's original shape. Analysis of SEM micrographs suggests that the PCL phase is in fact degrading, lending support to the hypothesized de-percolation of PCL. This theory is supported by the observed decrease in the heat of crystallization of PCL over time, a decrease from 9.031 to 0 W/g over 7 days for the 50:50 PCL:PELLETHANE® fiber composite. In addition, the PCL control samples degrade within 2 days, compared to the 5 days required to observe sample recovery in the programmed fiber composites. These findings suggest that the presence of PELLETHANE® in the composite samples inhibits the ability of the lipase to diffuse into the fiber composites and degrade the PCL shape fixing component and, further, that the mechanism of degradation is not mass loss but loss of crystallinity and concomitant softening of the PCL-based fixing phase.

A potential limitation of this first instantiation of the new SMP design is the relatively long time and high enzyme concentration required for enzymatic shape recovery. Few cell types may release enzyme at concentrations necessary for enzymatic shape recovery to occur in time-spans less than weeks or months. Because we speculate that the present material composition would recover in low enzyme concentrations, but over long time periods, the present composition may be best suited for applications in which slow response is beneficial or for applications in which cells, such as macrophages or hepatic cells, secrete high concentrations of enzyme. It is anticipated that the new SMP design could be adapted for more rapid recovery and/or low enzyme concentration triggering by increasing the enzymatic sensitivity of the labile fixing component. Conversely, even more gradual recovery than that demonstrated here could be achieved by decreasing enzymatic sensitivity of the labile fixing component. More generally, enzymatically responsive SMPs could, in theory, be designed to be triggered by any arbitrary enzyme by engineering the enzyme's target sequence into the polymer, though risk of cytotoxicity would likely be a constraint for many candidate enzymes.

In addition to contributing to SMP science, the present invention adds SMPs to the field of enzyme responsive materials (ERMs)—materials that undergo a material action, such as self-assembly/disassembly, transformation of surface properties, or swelling/deswelling, in response to enzymatic activity. ERMs have gained increasing attention due to the extreme specificity with which they can be designed to respond to the biological environment. In addition to bringing shape-changing functionality to the field of ERMs, the SMP design of the present invention represents the first SMP that could respond directly to biological activity. The majority of cell culture compatible SMPs have been thermally or photother-mally triggered. Dependence on these triggers prevents application as stimuli responsive materials designed to respond directly to biological activity. With the advent of enzymatically triggered SMPs, SMPs can now be designed for such applications.

What is claimed is:

1. A shape memory polymer system, comprising:
a composite fiber mat formed from at least a first set of fibers that are intermingled with a second set of fibers that has an initial shape;
wherein the first set of fibers are formed from a first polymer having a transition temperature such that the fiber web can be fixed into a temporary shape that is different than the initial shape when the fiber web is above the transition temperature and will remain in the temporary shape when the fiber web is below the transition temperature;
wherein the second set of fibers are formed from a second polymer that applies a biasing force to the first set of fibers when the fiber web is fixed into the temporary shape and the fiber web is below the transition temperature; and
wherein the first polymer is degradable by an enzyme and the second polymer is not degradable by the enzyme.

2. The shape memory polymer system of claim 1, wherein the first polymer is a polyester.

3. The shape memory polymer system of claim 2, wherein the first polymer is poly(ε-caprolactone).

4. The shape memory polymer system of claim 3, wherein the second polymer is a thermoplastic elastomer.

5. The shape memory polymer system of claim 4, wherein the second polymer is an aromatic polyether-based thermoplastic polyurethane.

6. The shape memory polymer system of claim 1, wherein the fiber web comprises between about 20 percent and about 50 percent poly(ε-caprolactone) by mass.

7. A method of forming a shape memory polymer system, comprising the steps of:
- providing a first polymer that is degradable by an enzyme and that has a transition temperature;
- providing a second polymer that is not degradable by the enzyme;
- dual electrospinning a first solution containing the first polymer with a second solution containing the second polymer to form a composite fiber mat formed at least a first set of fibers of the first polymer intermingled with at least a second set of fibers of the second polymer and that has an initial shape;
- heating the composite fiber mat above the transition temperature of the first polymer; and
- fixing the composite fiber mat into a temporary shape that is different than the initial shape so that the second set of fibers are applying a biasing force to the first set of fibers.

8. The method of claim 7, further comprising the step of exposing the composite fiber mat to the enzyme so that the first set of fibers are degraded and the composite fiber mat returns to the initial shape.

9. The method of claim 8, wherein the first polymer is poly($\varepsilon$-caprolactone).

10. The method of claim 9, wherein the second polymer is a thermoplastic elastomer.

11. The method of claim 10, wherein the second polymer is an aromatic polyether-based thermoplastic polyurethane.

12. The method of claim 11, wherein the fiber web comprises between about 20 percent and about 50 percent of poly($\varepsilon$-caprolactone) by mass.

* * * * *